United States Patent [19]

Jacobs

[11] Patent Number: 4,886,899
[45] Date of Patent: Dec. 12, 1989

[54] HOUSEFLY CHEMOSTERILANTS

[75] Inventor: Martin J. Jacobs, Terre Haute, Ind.

[73] Assignee: Pitman-Moore, Inc., Terre Haute, Ind.

[21] Appl. No.: 215,873

[22] Filed: Jul. 5, 1988

[51] Int. Cl.$^4$ ............................................. C07C 69/76
[52] U.S. Cl. ..................................... 560/064; 560/066
[58] Field of Search .................... 560/64, 66; 514/544

[56] References Cited

U.S. PATENT DOCUMENTS

| | | | |
|---|---|---|---|
| 1,953,629 | 3/1934 | Pfaff | 167/39 |
| 1,974,689 | 9/1934 | Pfaff et al. | 167/30 |
| 3,196,019 | 7/1965 | Andrews et al. | 99/2 |
| 3,239,341 | 3/1966 | Hodge et al. | 99/2 |
| 3,239,345 | 3/1966 | Hodge et al. | 99/2 |
| 3,239,346 | 3/1966 | Hodge et al. | 99/2 |
| 3,239,348 | 3/1966 | Hodge et al. | 99/2 |
| 3,239,354 | 3/1966 | Hodge et al. | 99/2 |
| 3,247,055 | 3/1966 | Gilbert | 167/30 |
| 3,760,040 | 9/1973 | Gutman | 260/941 |
| 3,860,616 | 1/1975 | Hoffsommer et al. | 260/343.2 |
| 3,996,349 | 12/1976 | Mulla et al. | 424/84 |
| 4,083,989 | 3/1978 | Kohn | 424/275 |
| 4,088,658 | 5/1978 | Edwin | 260/343 |
| 4,409,392 | 11/1983 | Hodge | 549/270 |
| 4,413,010 | 11/1983 | Zurfluh | 424/300 |
| 4,443,470 | 3/1984 | Hodge et al. | 424/279 |

OTHER PUBLICATIONS

Hidy et al., "Zearalenone and Some Derivatives: Production and Biological Activities", *Adv. Appl. Microbiol.*, 22:59-82 (1977).

Shipchandler, "Chemistry of Zearalanone and Some of Its Derivatives", *Heterocycles*, 3(6):471-520 (1975).

Peters et al., "A Stereoselective Synthetic Route to (R)-Zearalanone", *J. Med. Chem.*, vol. 18, No. 2, 215-17(1975).

Kuo et al., "The Resolution of ( )-Zearalenon. Determination of the Absolute Configuration of the Natural Enantiomorph", *Chemical Communications*, p761 (1967).

*Primary Examiner*—Paul J. Killos
*Attorney, Agent, or Firm*—Wendell R. Guffey; Thomas L. Farquer

[57] ABSTRACT

Substituted resorcyclic acid esters having the structural formula:

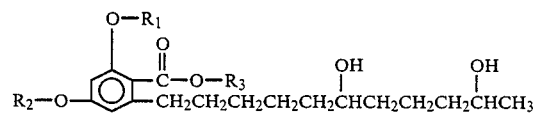

wherein $R_1$ and $R_2$, which may be the same or different, are H, X, or COX, where X is an alkyl group having from 1-6 carbon atoms; and $R_3$ is an alkyl group having from 1-12 carbon atoms are synthesized and used as housefly chemosterilants which reduce housefly fecundity.

20 Claims, No Drawings

HOUSEFLY CHEMOSTERILANTS

This invention relates generally to methods for controlling undesirable housefly (*Musca domestica*) reproduction and population and particularly to a method using substituted resorcylic acid esters as housefly chemosterilants which reduce housefly fecundity.

BACKGROUND OF THE INVENTION

Zearalenone and its derivatives are the basic Resorcylic Acid Lactone (RAL) compounds used as the starting materials for the compounds of the present invention. Zearalenone may be prepared by culturing the zearalenone producing strain of *Gibberella zeae* as taught in U.S. Pat. No. 3,196,019, incorporated herein by reference. Zearalenone and its ring-opened and other derivatives have been reviewed in the literature. Shipchandler, *Heterocycles*, 3(6):471–520 (1975) and Hidy et al "Zearalenone and Some Derivatives: Production and Biological Activities", *Adv. Appl. Microbiol.*, 22:59–82 (1977).

Zearalenone has been chemically modified to form numerous derivatives. U.S. Pat. No. 3,239,348, incorporated herein by reference, discloses a method for producing zearalenol from zearalenone by reducing the ketone carbonyl group. U.S. Pat. No. 3,239,345, incorporated herein by reference, discloses a method for producing zearalanol and its derivatives from zearalenone and zearalenol by reducing the ketone carbonyl group and/or the macrocylic ring double bond. U.S. Pat. No. 4,690,948, incorporated herein by reference, discloses a method for producing ring opened compounds from zearalanol and its derivatives. Numerous other patents and literature references detailing methods for preparing derivatives of zearalenone, zearalenol, and zearalanol are known in the art.

These compounds have generally been used to improve growth performance in animals. These compounds, however, have not previously been shown to be insect chemosterilants.

Numerous insecticides which affect the survivability and reproducibility of houseflies are known. For example, U.S. Pat. No. 1,974,689 discloses esterified carboxyl compounds useful for killing or eliminating flies; U.S. Pat. No. 3,247,055 discloses the use of triphenyltin compounds to control the ability of houseflies to effect sterilization during mating; U.S. Pat. No. 4,515,808 discloses organic compounds useful for combatting infestation with houseflies; U.S. Pat. No. 4,535,076 discloses organophosphate pesticides useful against houseflies; and U.S. Pat. No. 4,413,010 discloses carbamic acid compounds useful against houseflies. Numerous other insecticides are known to those skilled in the art.

There is a continuing need for new compounds that can reduce insect reproduction and therefore control the insect population, particularly the common housefly (*Musca domestica*).

SUMMARY OF THE INVENTION

It is, therefore, an object of the present invention to provide a method for controlling housefly reproduction.

It is another object of the present invention to provide a method for reducing housefly fecundity.

It is another object of the present invention to provide a chemosterilant which controls housefly reproduction by reducing housefly fecundity.

These and other objects are achieved by synthesizing housefly chemosterilants comprising substituted resorcylic acid esters and feeding the chemosterilants to houseflies to reduce housefly fecundity. The chemosterilants of the present invention have the structural formula:

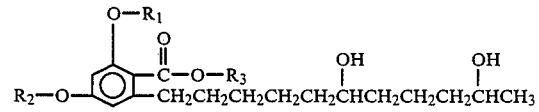

wherein $R_1$ and $R_2$, which may be the same or different, are H, X, or COX, where X is an alkyl group having from 1–6 carbon atoms; and $R_3$ is an alkyl group having from 1–12 carbon atoms.

Preferably, $R_1$ and $R_2$ are H, $CH_3$, or $COCH_3$; and $R_3$ is an alkyl group having from 5–9 carbon atoms.

In the most preferred compound, $R_1$ and $R_2$ are H and $R_3$ is an alkyl group having 8 carbon atoms; n-octyl-2[6R,10S]-6,10-dihydroxyundecyl-4,6-dihydroxybenzoate.

The chemosterilants are fed to houseflies by making available ad libitum a feed containing the chemosterilant in amounts of from about 1–10% by weight. The houseflies consume the chemosterilant along with the feed; the chemosterilant reduces fecundity and thereby controls housefly reproduction and population.

Other objects, advantages, and novel features of the present invention will become apparent from the following detailed description of the invention.

DETAILED DESCRIPTION OF THE INVENTION

As used herein, the term "chemosterilant" is defined to mean a compound which reduces the fecundity of the housefly. The term does not include compounds which reduce the ability of the housefly to effect fertilization during mating.

As used herein, the term "insecticide" is defined to mean a compound which reduces the ability of an insect to effect fertilization during mating or which kills insects. The term does not include compounds which reduce fecundity of the housefly.

In accordance with the present invention, substituted resorcylic acid esters are synthesized and used as housefly chemosterilants which reduces housefly fecundity. The chemosterilants have the structural formula:

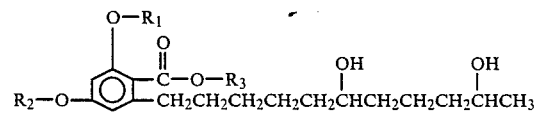

wherein $R_1$ and $R_2$, which may be the same or different, are H, X, or COX, where X is an alkyl group having from 1–6 carbon atoms; and $R_3$ is an alkyl group having from 1–12 carbon atoms.

Preferably, $R_1$ and $R_2$ are H, $CH_3$, or $COCH_3$; and $R_3$ is an alkyl group having from 5–9 carbon atoms.

In the most preferred compound, $R_1$ and $R_2$ are H and $R_3$ is an alkyl group having 8 carbon atoms; n-octyl-2[6R,10S]-6,10-dihydroxyundecyl-4,6-dihydroxybenzoate.

The chemosterilants are formed by reacting zearalanol and its derivatives directly with alkyl alcohols.

Typically, zearalanol or one of its derivatives is mixed with an alkyl alcohol, heated to temperature of from about 100°-250° C. for a period of from about 8-48 hours, and treated to separate the desired ester from the reaction mixture.

The chemosterilants are fed to houseflies by making available ad libitum a feed containing the chemosterilant. The houseflies consume the chemosterilant along with the feed; the chemosterilant reduces fecundity and thereby controls housefly reproduction and population.

The amount of chemosterilant fed to the housefly is dependent upon factors such as environmental and climatic conditions, housefly population, housefly fecundative capabilities, and the like. Generally, a chemosterilant concentration of from about 0.1-10%, preferably from about 1-5%, percent by weight based on the amount of feed employed reduces the fecundity and controls housefly reproduction and population.

The feed employed is a substance to which the housefly is attracted; any substance may be employed provided its properties present a desirable substance which the housefly consumes. The feed may comprise non-fat dry milk, granulated sugar, powdered eggs, malt, molasses, yeast, or other feeding sources or combinations thereof having incorporated into such feed the chemosterilant of the present invention. A 1:1 mixture of sugar and low-fat dried milk in which the dry chemosterilant had been thoroughly mixed at concentration of 2% by weight (20 mg/g) is conveniently employed. Numerous such feeds are known in the art.

The physical form of such feed is not critical and may be any form suitable for making the feed readily available for the housefly. Preferably, the feed is in a form that can be easily introduced into the housefly's environment, typically a solution or solid containing the chemosterilant.

A feed solution may be prepared by dissolving the chemosterilant in an appropriate solvent, typically water although other solvents such as various alcohols and organic solvents may be used. Preferably, the solution feed should contain an alluring substance, although not necessarily of nutritious value, which will attract the houseflies to the feed. The solution may be introduced into the environment by conventional means such as spraying or pouring.

A solid feed may be prepared by admixing the solid chemosterilant with the feed in the appropriate amounts or by dissolving the chemosterilant in a suitable solvent, applying the appropriate amount of solution to a feed, removing the solvent by distillation or evaporation, and isolating the feed containing the chemosterilant. Preferably, the solid feed should contain an alluring substance which is coated or impregnated in the feed with the chemosterilant. The feed may be introduced into the environment by conventional means such as dispersing the feed in the form of dust, granules or making available the feed in bait-traps or bait dispensers. For application as a dust or as granules, the treated feed is pulverized by conventional means. Many bait-traps and feed dispensers are known in the art; e.g. U.S. Pat. No. 4,639,393, incorporated herein by reference, discloses a dispenser useful for controlled release of chemosterilants such as those of the present invention.

According to the present invention, a composition of matter comprising an insecticide and the chemosterilant of the present invention is fed to houseflies to control the housefly population. The insecticide reduces the ability of the adults to reproduce or survive and the chemosterilant reduces the fecundity.

The insecticide can be any compound which reduces the ability of houseflies to effect fertilization or which kills houseflies. Numerous such compounds are known in the art, particularly carbamate and organophosphate insecticides.

The composition is fed to houseflies by making available ad libitum a desirable feed containing the composition. The houseflies consume the composition along with the feed; the insecticide reduces the ability of the housefly to effect fertilization during mating or which kills houseflies and the chemosterilant reduces fecundity. The combination of the insecticide and the chemosterilant of the present invention effectively controls the housefly population by effecting both the survivability and reproducibility of the housefly.

The amount of composition fed to the housefly is dependent upon factors such as environmental and climatic conditions, housefly population, housefly fecundative capabilities, housefly reproductive capabilities, and the like and particularly upon the insecticide used to form the composition. Generally, a chemosterilant concentration of from about 0.1-10%, preferably from about 1-5%, and an insecticide concentration of from about 0.1-10% by weight based on the amount of feed employed reduces the fecundity and controls housefly reproduction and population. It must be emphasized, however, that the weight percent for the insecticide is only an estimate and would depend upon the characteristics of the insecticide.

The composition is incorporated into the feed as described for the chemosterilant above.

The invention having been generally described, the following examples are given as particular embodiments of the invention and to demonstrate the practice and advantages thereof. U.S. Pat. Nos., 3,196,019, 3,239,345, 3,239,348 and 4,690,948, incorporated herein by reference, disclose methods for producing zearalenone, zearalenol, zearalanol, and various esters and other derivatives of those compounds. These compounds and their derivatives as well as other compounds and derivatives well known in the art are used to produce the chemosterilants of the present invention. It is understood that the examples are given by way of illustration and are not intended to limit the Specification or the Claims to follow in any manner. In particular, the Specification and Claims as written are intended to include all isomers of the chemosterilants and the alkyl groups are intended to include linear and branched chains.

EXAMPLE 1

Synthesis of n-octyl-2[6R,10S]-6,10-dihydroxyundecyl-4,6-dihydroxybenzoate

A solution of alpha-zearalanol (9.61 grams, 0.030 moles) in octyl alcohol (50 milliliters, 41.35 grams, 0.32 moles) was warmed to 170° C. The reaction mixture was held at this temperature until thin-layer chromatography (silica, 3:1 hexane-acetone) indicated complete reaction (35 hours). At the end of this time, the volatile components were removed at reduced pressure. The residue was recrystallized three times from benzene to give 3.0 grams of an off-white solid with a melting point of 81°-84° C.; n-octyl-2[6R,10S]-6,10-dihydroxyundecyl-4,6-dihydroxybenzoate. The proton and carbon (decoupled) nuclear magnetic resonance spectrums were both consistent with the anticipated structure. The elemental analysis, shown in Table 1, was also consistent with the above structure; $C_{26}H_{44}O_6$.

EXAMPLE 2

Adult flies from a standard susceptible strain were separated by sex within 24 hours of emergence from the pupa to ensure that mating did not occur prior to exposure to the test chemosterilant. Ten flies of each sex were placed in a 5 ounce clear plastic cup with ventilation. The flies were provided with a 1:1 mixture of sugar and low-fat dried milk in which the dry chemosterilant had been thoroughly mixed at 2% final concentration (20 mg/g). Free access to water was provided. After 4 days, the flies were briefly subdued by cold treatment and a small container with damp Chemical Speciality Manufacturing Association (CSMA) medium (Purina fly larva medium #5060) was inserted for oviposition. After a further 24 hours these oviposition cups were removed and transferred to a larger batch of CSMA medium in a 5 ounce plastic cup where larval development was completed. The resulting pupae were collected and placed in cages for hatching. The number of adult flies emerging was counted. Flies were exposed to four different concentrations of the compound (5, 10, 20 and 50 mg/g diet) in duplicate. Negative controls were run in the absence of compound and a positive control (indomethacin at 20 mg/g) was included. The results are shown in Table 2.

Referring to Table 2, the positive control, indomethacin, reduced reproduction by about 85%. n-octyl-2[6R,10S]-6,10-dihydroxyundecyl-4,6-dihydroxybenzoate reduced reproduction, as compared to the untreated control, by about 12, 95, 68 and 68% for dosages of 5, 10, 15 and 20 mg/g diet, respectively. Replicates in this experiment were reasonably close in most cases. However, the dose-response relationship is unexpected. All concentrations of the compound decreased reproductive success, but the greatest effect was seen at an intermediate dose (10 mg/g). While such non-linear dose-response curves are not unknown, they are rare, and the most likely explanation rests on the variability of the bioassay.

TABLE 1

| Theoretical | Found |
|---|---|
| % C 68.99 | 69.09 |
| % H 9.80 | 9.88 |
| % O 21.21 | 21.03 |

TABLE 2

| Compound* | Concentration (mg/g) | No. Flies Emerging | Mean No. |
|---|---|---|---|
| Control | — | 156, 184 | 171 |
| Indomethacin | | 26, ** | 26 |
| Compound | 5 | 145, 155 | 150 |
| Compound | 10 | 9, 7 | 8 |
| Compound | 20 | 92, 19 | 56 |
| Compound | 50 | 50, 59 | 55 |

*n-octyl-2[6R,10S]-6,10-dihydroxyundecyl-4,6-dihydroxybenzoate
**Assay lost.

I claim:

1. A compound having the formula:

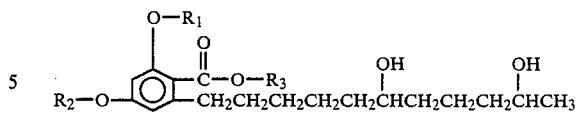

wherein $R_1$ and $R_2$, which may be the same or different, are H, X, or COX, where X is an alkyl group having from 1–6 carbon atoms; and $R_3$ is an alkyl group having from 1–12 carbon atoms.

2. The compound of claim 1 wherein $R_1$ and $R_2$ are H, $CH_3$, or $COCH_3$; and $R_3$ is an alkyl group having from 5–9 carbon atoms.

3. The compound of claim 1 wherein $R_1$ and $R_2$ are H and $R_3$ is an alkyl group having 8 carbon atoms; n-octyl-2[6R,10S]-6,10-dihydroxyundecyl-4,6-dihydroxybenzoate.

4. A method for controlling housefly reproduction and population by reducing housefly fecundity, comprising:
   feeding to said housefly a feed containing a fecundity reducing amount of a compound having the formula:

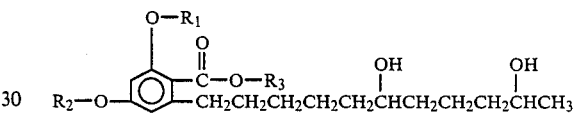

wherein $R_1$ and $R_2$, which may be the same or different, are H, X, or COX, where X is an alkyl group having from 1–6 carbon atoms; and $R_3$ is an alkyl group having from 1–12 carbon atoms.

5. The method of claim 4 wherein $R_1$ and $R_2$ are H, $CH_3$, or $COCH_3$; and $R_3$ is an alkyl group having from 5–9 carbon atoms.

6. The method of claim 4 wherein $R_1$ and $R_2$ are H and $R_3$ is an alkyl group having 8 carbon atoms; n-octyl-2[6R,10S]-6,10-dihydroxyundecyl-4,6-dihydroxybenzoate.

7. The method of claim 4 wherein said feed contains said compound in amounts of from about 0.1–10% by weight.

8. The method of claim 4 wherein said feed contains an alluring substance.

9. The method of claim 4 wherein said feed is in the form of a solution.

10. The method of claim 4 wherein said feed is in the form of a solid feed.

11. The method of claim 10 wherein said feed is a 1:1 mixture of sugar and low-fat dried milk.

12. The method of claim 10 wherein said feed contains said compound at about a 2% final concentration.

13. A composition suitable for reducing housefly population, comprising:
   a compound having the formula:

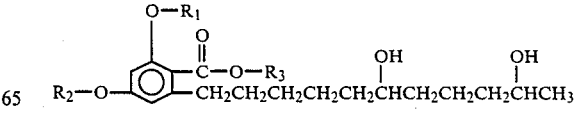

wherein $R_1$ and $R_2$, which may be the same or different, are H, X, or COX, where X is an alkyl group having from 1-6 carbon atoms; and $R_3$ is an alkyl group having from 1-12 carbon atoms; and an insecticide.

14. The composition of claim 13 having a compound wherein $R_1$ and $R_2$ are H, $CH_3$, or $COCH_3$; and $R_3$ is an alkyl group having from 5-9 carbon atoms.

15. The composition of claim 13 having a compound wherein $R_1$ and $R_2$ are H and $R_3$ is an alkyl group having 8 carbon atoms; n-octyl-2[6R,10S]-6,10-dihydroxyundecyl-4,6-dihydroxybenzoate.

16. The composition of claim 13 in the form of a feed composition further comprising a desirable housefly feed.

17. The composition of claim 14 wherein said feed contains said compound and said insecticide in amounts of from about 0.1-10% by weight.

18. The composition of claim 14 wherein said feed is in the form of a solution.

19. The composition of claim 14 wherein said feed is in the form of a solid feed.

20. The composition of claim 19 wherein said feed is a 1:1 mixture of sugar and low-fat dried milk containing said compound at about a 2% final concentration.

* * * * *